United States Patent [19]

Troyer

[11] Patent Number: 4,594,810
[45] Date of Patent: Jun. 17, 1986

[54] INBRED CORN LINE

[75] Inventor: A. Forrest Troyer, DeKalb, Ill.

[73] Assignee: DeKalb Pfizer Genetics, DeKalb, Ill.

[21] Appl. No.: 703,589

[22] Filed: Feb. 21, 1985

[51] Int. Cl.⁴ .............................................. A01H 1/02
[52] U.S. Cl. ......................................................... 47/58
[58] Field of Search ............................................. 47/58

[56] References Cited

U.S. PATENT DOCUMENTS

| | | | |
|---|---|---|---|
| 3,710,511 | 1/1973 | Patterson | 47/58 |
| 4,051,629 | 10/1977 | Galinat | 47/58 |
| 4,237,652 | 12/1980 | Rothermel | 47/58 |
| 4,368,592 | 1/1983 | Welch | 47/58 |

*Primary Examiner*—Robert E. Bagwill
*Attorney, Agent, or Firm*—Sughrue, Mion, Zinn, Macpeak & Seas

[57] ABSTRACT

This invention relates to an inbred line of corn having the designation HBA1, seeds produced by plants of the inbred line HBA1, cells which upon growth and differentiation produce the inbred line HBA1, hybrid corn seed produced by crossing the inbred line HBA1 with another corn line and a process for the production of hybrid corn seed using the inbred line HBA1.

10 Claims, No Drawings

INBRED CORN LINE

FIELD OF THE INVENTION

This invention relates to an inbred line of corn having the designation HBA1, seeds produced by plants of the inbred HBA1, cells which upon growth and differentiation produce the inbred line HBA1, hybrid corn seed produced by crossing the inbred line HBA1 with another corn line and a process for the production of hybrid corn seed using the inbred line HBA1.

BACKGROUND OF THE INVENTION

*Zea mays* or corn is an agronomically important crop in many countries of the world and is extremely commercially important in the United States. Corn is used for feed, for food and for industrial purposes.

Within the past 60 years, hybrid corn has become commercially dominant. As a result of the hybridization of corn, varieties with markedly improved yields, better stalks, better roots, markedly more uniform characteristics, and improved resistance to insect and disease pests have been developed.

Single cross hybrid corn is produced by using a homozygous inbred line as the parent. Homozygosity in an inbred line is achieved by repeated inbreeding and in general, by the sixth or seventh generation the inbred line is considered genetically pure. Unfortunately, a reduction in performance, yield and other plant characteristics, which are desirable, arises as a result of the inbreeding to achieve essentially genetic identity. As a result, these inbred corn lines are not grown as a commercial crop.

Although inbred lines which have been developed by various breeders in corn research are not grown as a commercial crop, they are extremely important because they are employed to produce first generation ($F_1$) hybrids by the hybridization of, for example, two inbred lines as parents. As a result of the crossing of the two inbred lines, hybrid vigor or heterosis arises and the hybrid plants produced have markedly improved yields, better stalks, better roots, better uniformity and better insect and disease resistance. Further, as a result of self-pollination of $F_1$ hybrid plants or cross-pollination of $F_1$ hybrid plants, a second generation ($F_2$) hybrid occurs due to the self-pollination or crosspollination of $F_1$ hybrid plants. The $F_2$ hybrid plant, and seed produced thereby, has characteristics which are less desirable than those of the $F_1$ hybrid, for example, lower yields, and expression of undesirable genetic traits results. Due to this reduced performance, seed from $F_1$ hybrids which produces less advantageous second generation $F_2$ hybrids is not saved by farmers. Rather, new hybrid seed produced by crossing the originally selected inbred parents to produce the first generation hybrid ($F_1$) seed is purchased from commercial seed companies by farmers each year for their planting.

The selection and production of inbred lines as parents which when crossed provide superior and improved $F_1$ hybrids is a specialized and highly skilled area. Not only must a corn breeder select and develop superior inbred parental lines, but the corn breeder must also be able to produce and select hybrid combinations of these inbred lines which will produce desirable $F_1$ hybrids which will be commercially successful.

As a result of the necessity to utilize inbred parental lines to produce commercially desirable and successful $F_1$ corn hybrids, great emphasis is placed in corn breeding and hybridization to develop the necessary inbred parental lines. As a result, it is essential to select and develop new inbred lines which when used in hybridization will provide improvements in first generation hybrid corn characteristics in terms of increased yield, improved plant stability, improved resistance to disease and other insect pests, uniformity in appearance to thereby permit easy mechanical harvesting and maximization of harvesting efforts with a minimization of labor involved, etc.

As a result, a concerted effort exists in the production of commercially successful first generation corn hybrids to develop the necessary inbred lines as parental stock.

SUMMARY OF THE INVENTION

Accordingly, an object of this invention is to provide a unique inbred line of corn having the designation HBA1.

A further object of this invention is to provide an inbred line with the designation HBA1 which has appropriate characteristics that when crossed, as a male parent or female parent, with another corn inbred, the first generation ($F_1$) hybrid thereby produced has advantageous and desirable characteristics.

Another object of this invention is to provide seed of the inbred line having the designation HBA1.

Also an object of this invention is to provide pollen of the inbred line HBA1 for fertilization of other varieties of corn to produce first generation ($F_1$) corn hybrids with excellent and improved characteristics.

An even further object of this invention is to provide a process for producing corn hybrids from inbred parental lines, one of which is the inbred line HBA1, where as a result of heterosis, first generation ($F_1$) hybrid corn with desirable characteristics such as high yield, better stability, improved insect resistance and disease resistance, and the like results.

These and other objects of the invention are achieved with an inbred line of corn having the designation HBA1 with superior yield, excellent stalks, and excellent stay-green characteristics.

This invention in another embodiment provides hybrid corn produced by crossing a first corn line with a second corn line, where the first corn line or the second corn line is the corn inbred line HBA1 and the other corn line is an inbred line of corn other than HBA1 or is a hybrid corn cross.

In a further embodiment of this invention, this invention provides seed of the inbred line HBA1.

In an even further embodiment of this invention, this invention provides pollen of the inbred line HBA1, useful in fertilization of other lines of corn to produce seed.

Also an embodiment of this invention is a process for producing a hybrid corn variety comprising:
(a) planting in pollinating proximity seeds of the inbred line HBA1 and seeds of another corn line;
(b) cultivating the corn plants resulting from the planting before the time of flowering;
(c) emasculating the plants of the other corn line;
(d) allowing cross-pollination to occur between the inbred line HBA1 and the other corn line; and
(e) harvesting seeds produced on the plants of the other corn line, with embodiments including the other corn line being a hybrid corn cross or an inbred corn line and with a particularly preferred embodiment being the use of another inbred corn line as the other corn line in the above process.

DETAILED DESCRIPTION OF THE INVENTION

As indicated above, this invention provides a novel inbred line HBA1 useful as a parental line by crossing with other corn lines, particularly corn inbred lines, to produce first generation ($F_1$) corn hybrids. Although generally the inbred line HBA1 is employed as a male parent in the cross-breeding, if desired, the inbred line HBA1 can be employed as a female parent.

The inbred corn line HBA1 is a yellow dent corn inbred line and was developed as indicated below:

A cross of hybrid lines 3195 (as the male) and 3199 (as the female), commercially available from Pioneer Hi-Bred, using conventional cross hybridization techniques was made. More specifically, seeds of the two lines were planted in pollinating proximity, the plants were grown to the stage of flowering, the female line 3199 pollinated by pollen from the male line 3195, and seed of this cross was saved. This seed was grown and the plants grown were selfed. More than a pound of the seed produced was saved. In a subsequent growing season, 600 plants were grown at high-plant density in 16 rows and were self-pollinated. Thirty-five self-pollinated ears from strong flowering plants with good stay-green characteristics were saved. Subsequently, in another growing season, 35-ear rows were grown and 4 self-pollinated ears from leaf disease-resistant plants (resistant to Northern leaf blight (*H. turcicum* L.), and Southern leaf blight (*H. maydis* L.)) were saved from ear 1.

Thereafter, in a subsequent growing season, 4 ears were grown and 1 self-pollinated ear from the most vigorous row was saved from ear 1. As a result of growing this 1 ear, 2 self-pollinated ears from leaf disease-resistant plants were saved. When they were subsequently grown in a later growing season, 7 self-pollinated ears in the most heat-tolerant row were saved.

Test crosses were then made to B73 and PA91, publicly known and available inbred corn lines, and to W72628, a proprietary inbred corn line, for evaluation of hybrid performance.

Further, 3 ears were grown from the 7 self-pollinated ears obtained from the previous growing season and 6 self-pollinated ears were saved from ear 1.

Thereafter, 6 ears were grown and found to be uniform, 12 ears were saved from ear 1 and the inbred line was given the designation HBA1. At this time, as a result of the selfing through eight generations, the inbred line HBA1 was considered to be essentially homozygous.

Seeds of this inbred line developed as a result of the above inbreeding have been deposited in American Type Culture Collection, Rockville, Maryland 20852, and have received accession No. 40225.

The cells of plants of inbred line HBA1 which can be grown in culture and differentiated or regenerated to form plants of the inbred line also constitute a part of this invention. For details of generation procedures see C. E. Green and C. A. Rhodes, "Plant Regeneration In Tissue Culture of Maize", 1982, *Maize for Biological Research*, ed. W. F. Sheridan, Plant Molecular Biology Association, Charlottesville, Va. pp.367–372.

As indicated above, inbred line HBA1 is a yellow dent corn appropriately adapted for growth in the South Central Region of the United States. This inbred line has the following characteristics:

Maturity

Days from emergence to 50% of plants in silk: 61 days/1446 heat units.
Days from 50% silk to harvest at 25% by weight kernel moisture: 81 days/1525 heat units.

Plant

Height (to tassel tip): 236 cm
Ear Height (to base of top ear): 72 cm
Length of Top Ear Internode: 14 cm
Number of Tillers: None
Number of Ears Per Stalk: Slight two-ear tendency
Cytoplasm type: Normal

Leaf

Color: Medium green (WF9)
Angle from Stalk: <30°
Sheath Pubescence: Light (W22)
Marginal Waves: Few (WF9)
Longitudinal Creases: Absent (OH51)
Width: Widest point of ear node leaf: 9 cm
Number of leaves per mature plant: 20
Length: ear node leaf, 83 cm

Tassel

Number of Lateral Branches: 9
Branch Angle from Central Spike: <30°
Penduncle Length (from top leaf to basal branches): 10 cm
Pollen Shed: Heavy (KY21)
Anther Color: Yellow
Glume Color: Green

Ear (Husked Ear Data Unless Otherwise Stated)

Length: 17 cm
Mid-point Diameter: 41 mm
Weight: 135 gm
Kernel Rows: 16; distinct; straight
Silk Color (exposed at Silking Stage): Violet
Husk color: Fresh/Medium Green; Dry/Buff
Husk Extension (Harvest Stage): Medium (Barely covering Ear)
Husk Leaf: Short (<8 cm)
Shank: 10 cm long; Internodes: 7
Taper: Average
Position at Dry Husk Stage: Upright
Drying Time (Unhusked Ear): Slow

Kernel (Dried)

Size (from Ear Mid-Point): 10 mm long; 8 mm, wide; 4 mm, thick
Shape Grade (% rounds): 60–80
Pericarp Color: Colorless
Aleurone Color: Homozygous; pale purple
Endosperm Color: Yellow
Endosperm Type: Normal Starch
Weight/100 Seeds (Unsized Sample): 30 gm

Cob

Diameter at Mid-point: 20 mm
Strength: Strong
Color: Red

Disease Resistance

Northern Leaf blight (Race 1 and 2): Resistant
*H. carbonum* (Race 2): Resistant
*H. carbonum* (Race 3): Resistant Southern Leaf Blight (Race 0): Resistant Insect Resistant Cornborer (1st Brood): Resistant
*Ostrinia Nubilalis* (2d Brood): Resistant Varieties Most Closely Resembling Corn Inbred Line HBA1 for the Characteristics Given:

| Character | Variety |
|---|---|
| Maturity | PA91 |
| Plant Type | PA91 |
| Ear Type | PA91 |
| Kernel Type | PA91 |

Heat units calculations are derived by using the following formula: GDD equals [Daily Maximum Temperature ($\leq 86°$ F.) plus Daily Minimum Temperature ($\geq 50°$ F.)] divided by 2 minus $50°$ F.

Inbred corn line HBA1 is a yellow dent corn inbred line. The closest known inbred line is PA91. However, inbred line HBA1 is statistically significantly different from known inbred line PA91 in terms of ear height (134.7 cm versus 132.2 cm), tassel branch number (8.9 versus 16.0) and tassel branch angle (28.3 degrees 42.3 degrees). Further, this inbred line has distinct characteristics in that the kernel row is more distinct than the kernel row of PA91 and is straighter than that of PA91.

These characteristics of inbred line HBA1 versus publicly known inbred line PA91 are summarized in Table 1 below:

TABLE 1

HBA1 versus PA91

| Ear Characteristics | HBA1 | PA91 | Testing Hypothesis Ho: $\mu_1 = \mu_2$ Ha: $\mu_1 \neq \mu_2$ |
|---|---|---|---|
| 1. Ear Length (cm) | $\overline{X}_1 = 16.6$ | $\overline{X}_2 = 17.1$ | Not Significant ($\alpha = 0.10$) |
| 2. Ear Diameter (cm) | $\overline{X}_1 = 4.1$ | $\overline{X}_2 = 3.9$ | Not Significant ($\alpha = 0.10$) |
| 3. Ear Weight (gm) | $\overline{X}_1 = 134.7$ | $\overline{X}_2 = 132.2$ | Significant ($\alpha = 0.10$) |
| 4. Tassel Branch Number | $\overline{X}_1 = 8.9$ | $\overline{X}_2 = 16.0$ | Significant ($\alpha = 0.10$) |
| 5. Number of Kernel Row | $\overline{X}_1 = 16.9$ | $\overline{X}_2 = 15.4$ | Not Significant ($\alpha = 0.10$) |
| 6. Tassel Branch Angle (°) | $\overline{X}_1 = 28.3°$ | $\overline{X}_2 = 42.3$ | Significant ($\alpha = 0.10$) |
| 7. Silk Color | Violet | Yellow | |

Note: $\eta_1 = \eta_2 = 100$

Isozyme analysis of inbred lines HBA1 and PA91 shows that genetic differences exist in at least three different loci, AcPH—2 versus 4; Idh B—6 versus 4 and PHI—5 versus 4.

Isozyme genotypes of inbred line HBA1 in comparison with known inbred lines B73 and PA91 are shown in Table 2 below:

TABLE 2

Isozyme Genotypes of HBA1

| Locus | Allelles Present | | |
|---|---|---|---|
| | HBA1 | B73 | PA91 |
| AcPH | 2 | 2 | 4 |
| ADH | 4 | 4 | 4 |
| Cat | 9 | 9 | 9 |
| EP | 6 | 6 | 6 |
| GOT U | 4 | 4 | 4 |
| GOT M | 4 | 4 | 4 |
| GOT L | 4 | 4 | 4 |
| B-Glu | 6 | 7 | 7 |
| MDH A | 6* | 6* | 6* |
| MDH B | 6 | 3.5 | 3.5 |
| MDH C | 16 | 16 | 16 |
| MDH D | 12 | 12 | 12 |
| MDH E | 12 | 12 | 12 |
| PGM A | 9 | 9 | 9 |
| PGM B | 4 | 4 | 4 |
| PHI | 5 | 4 | 4 |
| # of Plants Assayed | 81 | 6 | 6 |

*Allele is probably 6 but null cannot be ruled out.
The technique of using isozymes for genotyping or "fingerprinting" is described in the following reference: Goodman, M. M. and C. M. Stuber, 1980, "Genetic Identification of Lines and Crosses Using Isoenzyme Electrophoresis". Proceedings of the Thirty-Fifth Annual Corn and Sorghum Industry Research Conference.

Inbred line HBA1 is an advantageous parental line for use in production of hybrid corn, particularly first generation ($F_1$) hybrid corn. Where this inbred line is employed, it is employed with another inbred line, for example, and the two inbred lines are cross-hybridized using conventional techniques. More specifically, two inbred lines as parents, one of which is the inbred line HBA1, are planted in pollinating proximity to each other. This can be achieved by planting the parental lines in alternating rows, in blocks or in any other convenient planting pattern. The plants of both lines are both allowed to grow until the time of flowering. Advantageously, during this growth stage, the plants are generally thinned at about the 3-leaf stage and are also in general treated with fertilizer and/or other agricultural chemicals as considered appropriate by the grower.

At the time of flowering, in the vent that inbred line HBA1 is employed as the male parent, the tassels of the other parental line are removed from all plants of the other parental line employed as the female parent line. The detasseling can be achieved manually but also can be done by machine if desired. Alternatively, chemical sterilization or conversion of the female parent by addition of a cytoplasmic male sterile trait can be used.

The lines are then allowed to continue to grow and natural cross-pollination occurs as a result of the action of wind which is normal in the pollination of grasses, including corn. As a result of the emasculation of the female parent line, all the pollen from the male parent line, e.g., HBA1, is available for pollination since tassels and thereby pollen bearing flowering parts have been previously removed from all plants of the inbred line being used as the female in the hybridization. Of course, it would be obvious during this hybridization procedure, the parental varieties are grown such that they are isolated from other corn fields to prevent any accidental contamination of pollen from foreign sources. Isolation techniques are well within the skill of those skilled in this art.

Both of the parent inbred lines of corn are allowed to continue to grow until maturity but only the ears from the female inbred line as a parent are harvested to obtain seeds of a novel $F_1$ hybrid corn. If desired, corn produced in the male parent variety can be harvested, e.g., for grain use, but these seeds are not useful as hybrid seeds.

The novel $F_1$ hybrid seed produced can then be planted in a subsequent growing season with the desirable characteristics in terms of $F_1$ hybrid corn plants providing improved grain yields being achieved.

The inbred line HBA1 has been employed to produce novel $F_1$ corn plants with markedly advantageous characteristics, i.e., by utilizing inbred line HBA1 as the male parent inbred line with publicly known and commercially available inbred line B73 as the female parent. This first generation ($F_1$) corn hybrid designated DK672 is the subject of a copending patent application Ser. No. 703,587, filed Feb 21, 1985, simultaneously herewith; the disclosure of which is herein incorporated by reference. Another advantageous crossing is of inbred HBA1 as the male parent line with a DeKalb-Pfizer Genetics proprietary inbred line M103A as the female parent. This first generation ($F_1$) corn hybrid designated EXP474 is the subject of a copending application Ser. No. 703,579, filed Feb. 21, 1985, simultaneously herewith, the disclosure of which is incorporated herein by reference.

The characteristics of first generation ($F_1$) hybrid DK672 and first generation ($F_1$) hybrid EXP474 in comparison with identically obtained results on a DeKalb-Pfizer Genetics commercial variety DK656, and DeKalb-Pfizer Genetics commercial variety T1230, respectively, both of which mature at a similar rate and thus are appropriate for comparison, are shown in Table 3 below.

TABLE 3

| Hybrid | Yield in Bushels | Kernel Moisture Percent | Plant Height Inches | Ear Height Inches | Stay Green | Not Stalk Lodged | Yield Moisture |
|---|---|---|---|---|---|---|---|
| DK672 | 133.1 | 22.4 | 98.8 | 48.3 | 131.6 | 106.1 | 104.8 |
| DK656 | 135.4 | 21.8 | 94.4 | 50.9 | 95.9 | 102.5 | 109.8 |
|  |  | * | * | * | * | * | * |
| EXP474 | 133 | 22.7 | 100 | 100 | 150 | 96 | 103 |
| T1230 | 130 | 23.8 | 98 | 99 | 78 | 89 | 96 |

* = Statistically significant at the 1% level.

From the above, it can be seen that the inbred line HBA1 provides advantageous breeding stock for use as a parental line, either as a male parent or as a female parent, to provide first generation hybrids with unique and desirable characteristics.

While the invention has been described in detail and with respect to specific embodiments thereof, it would be apparent to one skilled in the art that various changes and modifications can be made therein without the departing from the spirit and scope thereof.

What is claimed is:

1. An inbred corn line having the designation HBA1.
2. A plant of the inbred corn line having the designation HBA1 of claim 1.
3. Seeds of the inbred corn line having the designation HBA1 of claim 1.
4. Pollen of the inbred corn line having the designation HBA1 of claim 1.
5. A plant cell which, upon growth and differentiation, produces the plant of claim 2.
6. First generation ($F_1$) hybrid corn seed produced by crossing a first inbred corn line as a male parent with a second inbred corn line as a female parent, one of said inbred corn lines being said inbred line HBA1.
7. The seed of claim 6, wherein said inbred line HBA1 is the male parent.
8. A process for producing hybrid corn comprising:
   (a) planting in pollinating proximity seeds of inbred corn line having the designation HBA1 of claim 1 and another line of corn;
   (b) cultivating corn plants resulting from the planting before the time of flowering;
   (c) emasculating the plants of either the inbred corn line HBA1 or of the other corn line;
   (d) allowing cross-pollination to occur between said corn lines and
   (e) harvesting seeds produced by said plants of the corn line which was emasculated in step (c).
9. The process of claim 8, wherein said other line of corn is an inbred line of corn other than said inbred corn line HBA1.
10. The process of claim 9, wherein said process comprises in step (c) emasculating the plants of said other line of corn.

* * * * *